(12) United States Patent
Estrada et al.

(10) Patent No.: US 11,861,894 B1
(45) Date of Patent: Jan. 2, 2024

(54) TARGET CUSTODY PLATFORM FOR MODELING TARGET NAVIGATION TRAJECTORY WITH CONFIDENCE INTERVALS

(71) Applicant: Royce Geospatial Consultants, Inc., Arlington, VA (US)

(72) Inventors: Adam Estrada, Reston, VA (US); Andrew Ryan, Baltimore, MD (US); Nick Thompson, Mosinee, WI (US); Matt Flure, Barboursville, VA (US); Casey Backes, O'Fallon, IL (US); Adam Ashurst, Warrenton, VA (US)

(73) Assignee: ROYCE GEOSPATIAL CONSULTANTS, INC., Arlington, VA (US)

( * ) Notice: Subject to any disclaimer, the term of this patent is extended or adjusted under 35 U.S.C. 154(b) by 0 days.

(21) Appl. No.: 18/357,965

(22) Filed: Jul. 24, 2023

Related U.S. Application Data

(60) Provisional application No. 63/500,269, filed on May 5, 2023.

(51) Int. Cl.
| | |
|---|---|
| *G06V 20/13* | (2022.01) |
| *G06T 7/62* | (2017.01) |
| *G06N 3/02* | (2006.01) |
| *G06N 3/08* | (2023.01) |
| *G06V 10/764* | (2022.01) |
| *G06V 10/62* | (2022.01) |

(52) U.S. Cl.
CPC .............. *G06V 20/13* (2022.01); *G06N 3/02* (2013.01); *G06N 3/08* (2013.01); *G06T 7/62* (2017.01); *G06V 10/764* (2022.01); *G06T 2207/20084* (2013.01); *G06T 2207/30241* (2013.01); *G06V 10/62* (2022.01)

(58) Field of Classification Search
CPC ...... G06V 20/13; G06V 10/764; G06V 10/62; G06N 3/02; G06N 3/08; G06T 7/62; G06T 2207/20084; G06T 2207/30241
See application file for complete search history.

(56) References Cited

U.S. PATENT DOCUMENTS 11,423,785 B2 * 8/2022 Fridman .................. G08G 3/00
2022/0091607 A1 * 3/2022 Zang ..................... B64C 39/024

* cited by examiner

*Primary Examiner* — Ankur Jain
(74) *Attorney, Agent, or Firm* — Galvin Patent Law LLC; Brian R. Galvin

(57) ABSTRACT

A target custody platform comprising a data acquisition engine, a data analysis engine, a machine learning engine, and a data presentation layer configured to task a plurality of satellites for imagery data wherein the imagery data and metadata is used in conjunction with other types of data including identification data and weather data as inputs into a one or more machine and/or deep learning algorithms configured to predict a the likelihood a target of interest will travel along a project path.

20 Claims, 9 Drawing Sheets

TARGET CUSTODY PLATFORM FOR MODELING TARGET NAVIGATION TRAJECTORY WITH CONFIDENCE INTERVALS

CROSS-REFERENCE TO RELATED APPLICATIONS

Priority is claimed in the application data sheet to the following patents or patent applications, each of which is expressly incorporated herein by reference in its entirety: 63/500,269

BACKGROUND OF THE INVENTION

Field of the Art

The present invention is in the field of predictive analytics, and more particularly in the field of intelligent target tracking and path projection.

Discussion of the State of the Art

What is needed is a platform which provides target custody tracking and which utilizes artificial intelligence to compute scores which indicate the confidence level of a target of interests projected path.

SUMMARY OF THE INVENTION

A target custody platform comprising a data acquisition engine, a data analysis engine, a machine learning engine, and a data presentation layer configured to task a plurality of satellites for imagery data wherein the imagery data and metadata is used in conjunction with other types of data including identification data and weather data as inputs into a one or more machine and/or deep learning algorithms configured to predict a the likelihood a target of interest will travel along a project path.

Accordingly, the inventor has conceived and reduced to practice, a target custody platform, comprising: a computing device comprising a memory and a processor; an analysis engine comprising a first plurality of programming instructions stored in the memory which, when operating on the processor, causes the computing device to: task a plurality of satellites with obtaining imagery data based on a projected path of a target of interest; build a plurality of satellite footprints using a subset of the imagery data; identify sections of the projected path where one or more of the satellite footprints intersect the projected path of the target of interest; for each identified section, calculate a cover area; calculate an amount of the projected path that the satellite footprints cover; and calculate an average ground sample distance based on a subset of the imagery data; and a machine learning algorithm configured to compute a confidence score for each of the identified sections based on input data comprising at least the plurality of satellite footprints, the identified sections, the calculated cover area for each section, the amount of the projected path that the satellite footprints cover, and the average ground sample distance.

According to another preferred embodiment, a method for providing target custody is disclosed, comprising the steps of: tasking a plurality of satellites with obtaining imagery data based on a projected path of a target of interest; building a plurality of satellite footprints using a subset of the imagery data; identifying sections of the projected path where one or more of the satellite footprints intersect the projected path of the target of interest; for each identified section, calculating a cover area; calculating an amount of the projected path that the satellite footprints cover; and calculating an average ground sample distance based on a subset of the imagery data; and using a machine learning algorithm configured to compute a confidence score for each of the identified sections based on input data comprising at least the plurality of satellite footprints, the identified sections, the calculated cover area for each section, the amount of the projected path that the satellite footprints cover, and the average ground sample distance.

According to an aspect of an embodiment, the machine learning algorithm is a random forest algorithm.

According to an aspect of an embodiment, the machine learning algorithm is a deep learning algorithm.

According to an aspect of an embodiment, the deep learning algorithm is a neural network.

According to an aspect of an embodiment,

According to an aspect of an embodiment, the analysis engine is further configured to: obtain a plurality of information associated with the target of interest from one or more external databases; determine a size of the target of interest based on the plurality of obtained information associated with the target; and wherein the size is used as an additional input into the machine learning algorithm.

According to an aspect of an embodiment, the analysis engine is further configured to: obtain weather pattern data; determine a cloud cover percentage based on the obtained weather pattern data; and wherein the cloud cover percentage is used as an additional input into the machine learning algorithm.

According to an aspect of an embodiment, the target of interest is a sailing vessel and wherein the information associated with the sailing vessel includes automated identification system data.

According to an aspect of an embodiment, the machine learning algorithm is a logistic regression algorithm.

According to an aspect of an embodiment, the target of interest is an airplane, a satellite, or a land vehicle.

According to an aspect of an embodiment, wherein each of the computed confidence scores for each of the identified sections are aggregated together to form an average confidence score for the entire projected path of the target of interest.

BRIEF DESCRIPTION OF THE DRAWING FIGURES

DETAILED DESCRIPTION OF THE INVENTION

Figure 1:
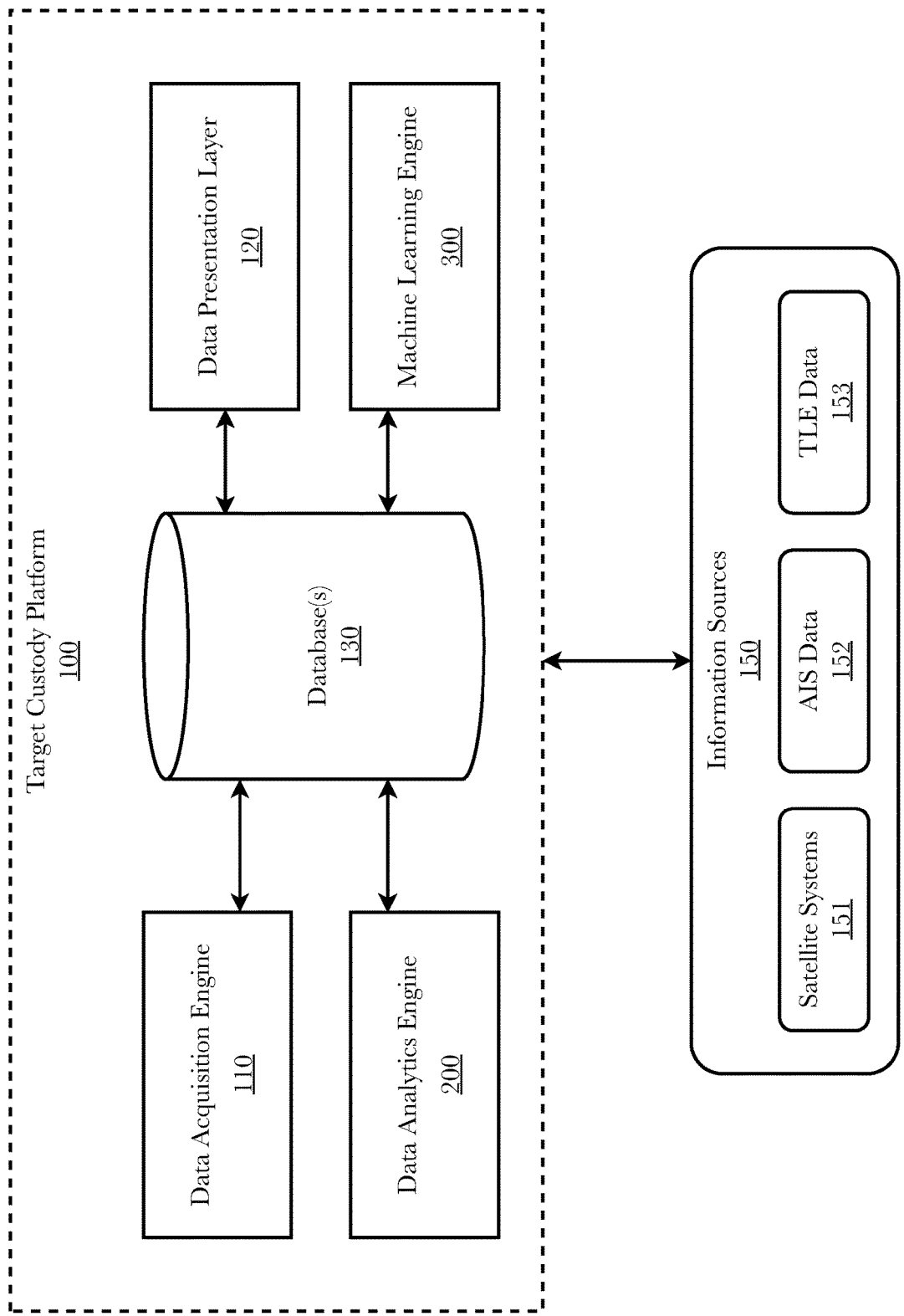
FIG. 1 is a block diagram illustrating an exemplary system architecture for a target custody platform, according to an embodiment.

The inventor has conceived, and reduced to practice, a target custody platform comprising a data acquisition engine, a data analysis engine, a machine learning engine, and a data presentation layer configured to task a plurality of satellites for imagery data wherein the imagery data and metadata is used in conjunction with other types of data including identification data and weather data as inputs into a one or more machine and/or deep learning algorithms configured to predict a the likelihood a target of interest will travel along a project path.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Conceptual Architecture

FIG. 1 is a block diagram illustrating an exemplary system architecture for a target custody platform 100, according to an embodiment. According to the embodiment, target custody platform 100 comprises a data acquisition engine 110, a data analytics engine 200, a data presentation layer 120, one or more databases 130, and a machine learning engine 300. In some implementations, target custody platform may be configured to operate on a computing device such as, for example, a server. In some implementations, target custody platform 100 may be configured as a cloud-based system and/or service accessible via a suitable network connection such as, for example, the Internet via a purpose-built software application or web application/interface. In some embodiments, platform 100 and one or more of its components may be operating on a single computing device or multiple computing devices communicatively coupled via a suitable network connection known to those skilled in the arts (i.e., local area network, wireless network, etc.).

According to various embodiments, target custody platform 100 can provide improved target tracking by leveraging machine learning and artificial intelligence for modeling target navigation channels (i.e., trajectory) with confidence intervals. In some implementations, the modeling methods can include an initial understanding of the confidence surrounding the expected trajectory, or navigation channels, of a target by category. Data acquisition engine 110 of target custody platform 100 can be configured to receive, retrieve, or otherwise obtain a plurality of data and information such as the exemplary information sources 150. Target custody platform 100 may interface with various information sources 150 using a suitable network connection. In some embodiments, data acquisition engine 110 may utilize various mechanisms, systems, or schemes for acquiring data. For example, data acquisition engine 110 may utilize one or more application programming interfaces (APIs) or API connectors configured to obtain data from a plurality of information sources 150. In one embodiment configured for tracking sailing vessels, an API may be used to query automated identification system (AIS) data 152 from a database which stores AIS data. As another example, an API may be used to acquire cloud cover data for a given location from one or more weather data sources such as, for example, National Oceanic and Atmospheric Administration (NOAA) national weather service database. In other embodiments, a web crawler may be implemented and configured to crawl websites which store relevant data. Data obtained by platform 100 can be stored in database(s) 130. Database(s) 130 may comprise one or more data storage devices and implement one or more data storage systems such as, for example, relational databases, non-relational databases, graph databases, object-oriented databases, centralized databases, distributed databases, and/or the like.

In various embodiments, target custody platform 100 may receive a target of interest as an input. In response, data acquisition engine 110 may task a plurality of satellites 151 with obtaining imagery data based on a projected path of the target of interest. According to some embodiments, the number and type of satellites tasked by custody tracking platform 100 may be at least partially based on the target of interest, a desired level of risk (i.e., the minimum amount of computed confidence), and derived features such as a predicted cone of trajectory. The imagery data may be stored in database(s) 130 and used by data analytics engine 200 to determine one or more satellite footprints.

According to the embodiment, data analytics engine 200 configured to provide various data processing and data analysis functions. In some embodiments, data analytics engine 200 obtains data from database(s) 130 and determines, computes, derives, or otherwise calculates one or more characteristics and/or features associated with a target of interest. According to some embodiments, the characteristics and/or features can include, but are not limited to, a channel cone, satellite footprints, target size (e.g., ship size determined by AIS data), number of possible footprints, cover area of a cone slice, cone/footprint convergence percentage, computed average ground slice distance, weather attributes, and/or the like. In some embodiments, the target of interest is a ship or sailing vessel. In other embodiments, the target of interest may be a truck, an airplane, a satellite, or any other object that can transit across a geographic region of the globe. Calculated features may be stored in database(s) 130. Calculated features determined by data analytics engine 200 can be fed as inputs into machine learning engine 300 which can utilize one or more machine and/or deep learning algorithms to train a model configured to determine a target of interest's likely trajectory using a computed confidence score.

According to the embodiment, machine learning engine 300 is configured to train, maintain, and deploy one or more machine and/or deep learning models to provide predictive target tracking capabilities. Machine learning engine 300 may receive, retrieve, or otherwise obtain a plurality of data which can be sourced from various information sources 150 including, but not limited to, satellite imagery data 151, data sourced from governmental and non-governmental organization databases, and "big data." For example, AIS data 152 and two-line element (TLE) data 153 from national and commercial sources (e.g., produced by NORAD, etc.) are a few such sources. Machine learning engine may use some or all of the obtained data to develop a model for tracking a target of interest.

According to the embodiment, a data presentation layer 120 is present and configured to provide a user interface for interacting with target custody platform 100. Data presentation layer 120 may be able to receive user queries and return an appropriate response, for example, by responding to a query for information by locating and retrieving the relevant information from database 130, or, as another example, by responding to an input target of interest by displaying, via a graphical user interface, a projection of the target vessel on a map with the cone of trajectory and its computed confidence levels displayed, as is described in more detail in FIG. 4 below. The presentation layer 120 may represent a front-end user interface for platform 100 and may be implemented as a web application or bespoke software application stored and operating on a computing device which utilizes the backend components of platform 100 to provide visual representations of queried data and predicted navigation channels. Data presentation layer 120 may obtain various data and implement one or more systems for visualizing and/or displaying the data. As a simple example, data may be obtained and then a graphing engine may be used to format the data for display as one or more various types of graphs (e.g., bar graphs, histograms, infographics, pie charts, etc.).

Figure 2:
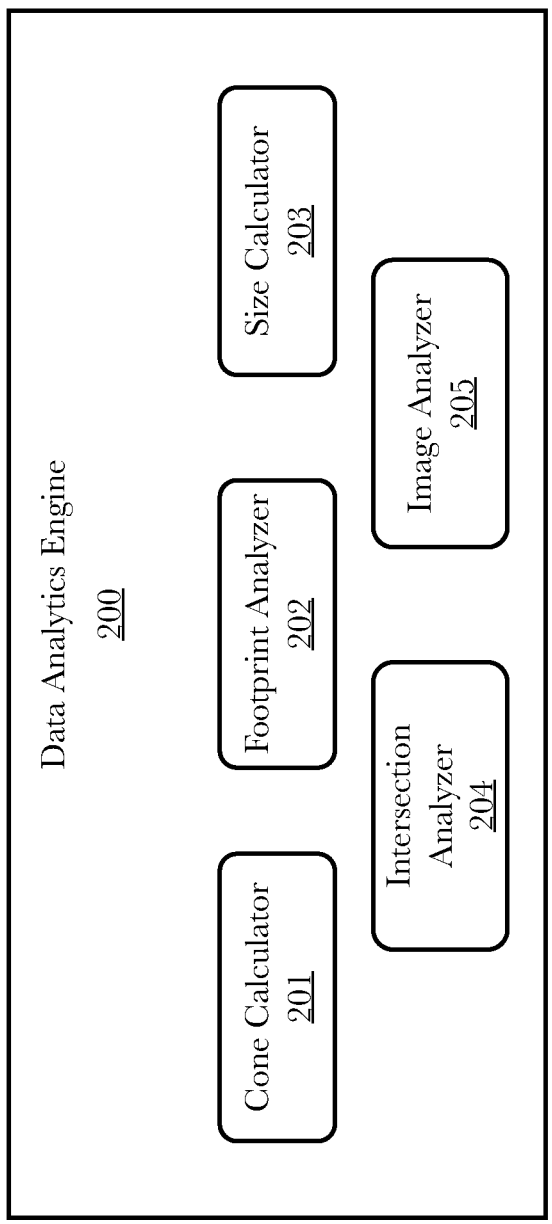
FIG. 2 is a block diagram illustrating an exemplary aspect of target custody platform, the data analytics engine.

FIG. 2 is a block diagram illustrating an exemplary aspect of target custody platform 100, the data analytics engine 200. According to the embodiment, data analytics engine 200 is configured to provide data processing and analysis functions to platform 100 and may comprise one or more modules configured to compute, derive, and/or calculate one or more characteristics and/or features associated with the target of interest. The first module that may be present is a cone calculator module 201 configured to process various information to determine a cone of trajectory for the target of interest. In a use case involving sailing vessels, data analytics engine 200 may process AIS data 152 to glean the location, heading, identity, and characteristics of a ship to produce a cone of trajectory.

A second module that may be present is a footprint analyzer 202 configured to receive a plurality of data from various data sources, including (but not limited to) TLE data 153, and build satellite footprints to project where the satellites will be at given points in time. TLE data is a data format encoding a list of orbital elements of an Earth-orbiting object for a given point in time, the epoch. Using a suitable prediction formula, the state (e.g., position and velocity) at any point in the past or future can be estimated to some accuracy. A satellite footprint is the ground area that its transponders offer coverage and determines the satellite dish diameter required to receive each transponders signals. Footprint analyzer 202 may further be configured to compare intersections between satellites (via the footprints) and the produced cone of trajectory and then calculate the number of possible footprints based on the section of cones available. Additional information that may be associated with or obtained from satellites can include, but is not limited to, the number of unique sensors, sensor types, sensor phenomenology, sensor ground sample distance (GSD), and sensor grazing angle.

Yet another module that may be present is a size calculator 203 module configured to determine the size of the target of interest. For example, in the use case of tracking sailing vessels, size calculator 203 may acquire ship dimension (e.g., length and width) from obtained AIS data 152. In some embodiments, targets of interest may need to be filtered by size.

An intersection analyzer module 204 may also be present and configured calculate the intersection over union between the area of the cone and the area of access windows for each. The intersection over union can be defined as the area of satellite access window overlap with the cone of trajectory divided by the area that the access window and cone occupy and/or overlap together. First, intersection analyzer module 204 may calculate the cover area of a single slice taken from the produced cone of trajectory. Next, intersection analyzer 204 may then calculate the percentage of the cone slice that the footprints (i.e., access windows) cover. This information may be used to compute the intersection over union between cone and satellite footprints.

According to various embodiments, image analyzer 205 may be configured to receive a plurality of imagery data and metadata from a plurality of satellite systems 151. Metadata can include, but is not limited to, the number of unique sensors, sensor types, sensor phenomenology, sensor GSD, and sensor grazing angle. Image analyzer 205 can be configured to calculate the average GSD of the satellite images per slice of the cone of trajectory.

Data analysis engine 200 uses these modules to derive characteristics (e.g., features) of the target of interest including, but not limited to, producing a cone of trajectory, building a plurality of satellite footprints using various data sources, determining target of interest size, calculating the number of possible footprints based on the section of cones available, calculating the cover area of a cone slice, calculating the percentage of the cone that the footprints cover, determining the average GSD per slice, and other data processing and analysis tasks that may be required to provide target custody capabilities. The derived characteristics and/or features may be stored in database(s) 130 and used as inputs by machine learning engine 300.

Figure 3:
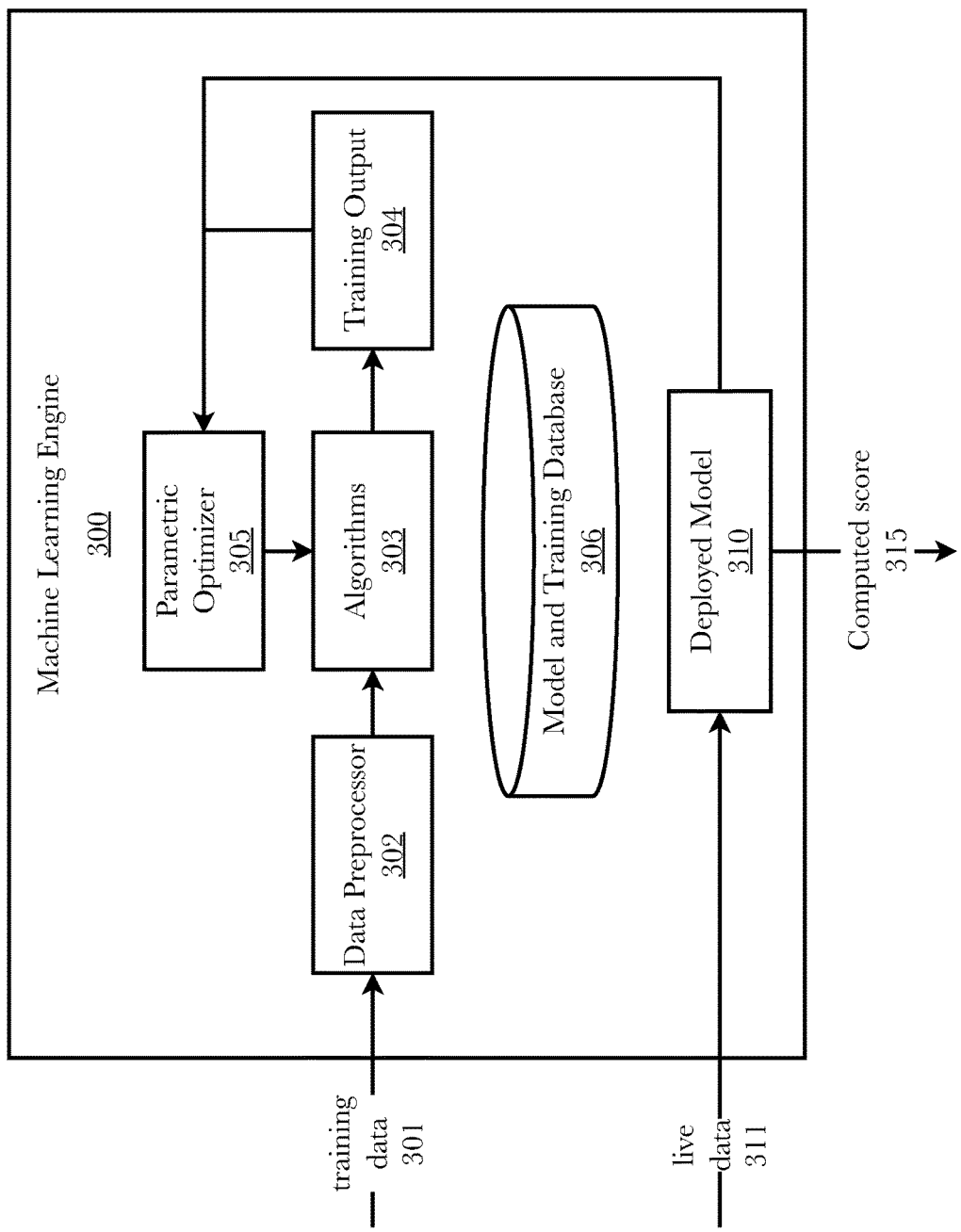
FIG. 3 is a block diagram illustrating an exemplary aspect of target custody platform, the machine learning engine.

FIG. 3 is a block diagram illustrating an exemplary aspect of target custody platform 100, the machine learning engine 300. According to the embodiment, machine learning engine may comprise a model training stage comprising a data preprocessor 302, one or more machine and/or deep learning algorithms 303, training output 304, and a parametric optimizer 305, and a model deployment stage comprising a deployed and fully trained model 310 configured to make predictions on live data 311.

At the model training stage, a plurality of training data 301 may be received at machine learning engine 300. In some embodiments, the plurality of training data may be obtained from one or more database(s) 130 and/or directly from various information sources 150 via data acquisition engine 110. In a use case directed to the tracking of ships at sea, a plurality of training data may be sourced from AIS databases. The training dataset may comprise a plurality of information including features and quantities derived, computed, or otherwise calculated by data analytics engine 200. For example, the training dataset and input data 301 may comprise variables such as the target size, target type (e.g., type of ship, type of airplane, type of truck, etc.), the total number of satellite access windows, access window intersection over union, number of sensors, sensor types, sensor phenomenology, average GSD, average grazing angle, average cloud coverage/cloud free percentage, and/or the like. Data preprocessor 302 may receive the input data and perform various data preprocessing tasks on the input data to format the data for further processing. For example, data preprocessing can include, but is not limited to, tasks related to data cleansing, data deduplication, data normalization, data transformation, handling missing values, feature extraction and selection, mismatch handling, and/or the like. Data preprocessor 302 may also be configured to create training dataset and a test set from the plurality of input data 301. For example, a training dataset may comprise 85% of the preprocessed input data and the test dataset may comprise the remaining 15% of the data. The preprocessed training dataset may be fed as input into one or more machine and/or deep learning algorithms 303 in order to train a predictive model for target custody tracking.

During model training, training output 304 is produced and used to measure the accuracy and usefulness of the predictive outputs. During this process a parametric optimizer 305 may be used to perform algorithmic tuning between model training iterations. Model parameters and hyperparameters can include, but are not limited to, bias, train-test split ratio, learning rate in optimization algorithms (e.g., gradient descent), choice of optimization algorithm (e.g., gradient descent, stochastic gradient descent, of Adam optimizer, etc.), choice of activation function in a neural network layer (e.g., Sigmoid, ReLu, Tanh, etc.), the choice of cost or loss function the model will use, number of hidden layers in a neural network, number of activation unites in each layer, the drop-out rate in a neural network, number of iterations (epochs) in a training the model, number of clusters in a clustering task, kernel or filter size in convolutional layers, pooling size, batch size, the coefficients (or weights) of linear or logistic regression models, cluster centroids, and/or the like. Parameters and hyperparameters may be tuned and then applied to the next round of model training. In this way, the training stage provides a machine learning training loop.

The test dataset can be used to test the accuracy of the model outputs. If the training model is making predictions that satisfy a certain criterion (e.g., baseline behavior, etc.), then it can be moved to the model deployment stage as a fully trained and deployed model 310 in a production environment making predictions based on live input data 311. The deployed model can output a computed score 315 indicating a confidence interval associated with a cone of trajectory for a target of interest. Further, model predictions made by deployed model can be used as feedback and applied to model training in the training stage, wherein the model is continuously learning over time using both training data and live data and predictions.

A model and training database 306 is present and configured to store training/test datasets and developed models. Database 306 may also store previous versions of models.

According to some embodiments, the one or more machine and/or deep learning models may comprise any suitable algorithm known to those with skill in the art including, but not limited to: supervised learning algorithms such as: regression (e.g., linear, polynomial, logistic, etc.), decision tree, random forest, k-nearest neighbor, support vector machines, Naïve-Bayes algorithm; unsupervised learning algorithms such as clustering algorithms, hidden Markov models, singular value decomposition, and/or the like. Alternatively, or additionally, algorithms 303 may comprise a deep learning algorithm such as neural networks (e.g., recurrent, convolutional, long short-term memory networks, etc.).

In some implementations, a neural network may be trained using preprocessed training data comprising at least in part, one or more of the features/variables and quantities determined by data analysis engine 200 or acquired from various information sources (e.g., AIS data 152). In such implementations, the neural network may consist of multiple layers of nodes: the input layer, the hidden layer, and the output layer. The input layer receives the input data and passes those past data values into the next layer. The hidden layer or layers have complex functions that create predictors. A set of nodes in the hidden layer called neurons represents math functions that modify the input layer. The output layer collects the predictions made in the hidden layer to produce the model's final prediction. The output layer may produce a weighted score that represents a confidence level associated with slice of a cone of trajectory per a given time frame (e.g., per hour, per half-hour, etc.). For example, at the input layer the neural network may receive a plurality of variables such, for example, the target size, target type (e.g., type of ship, type of airplane, type of truck, etc.), the total number of satellite access windows, access window intersection over union, number of sensors, sensor types, sensor phenomenology, average GSD, average grazing angle, average cloud coverage/cloud free percentage. These variables are passed into the hidden layer where weighting factors are applied to the variable nodes and the neural network outputs a computed score per hour of cone. In some implementations, the output may be a value between 0 and 1, inclusive, which represents a confidence value indicative of the model's confidence that a given slice of cone for a target of interest accurately represents the target's most likely navigation trajectory per some given period of time (e.g., per 60 minutes, 30 minutes, etc.).

In some implementations, algorithms 303 may comprise a random forest model trained using preprocessed training data comprising at least in part, one or more of the features/variables and quantities determined by data analysis engine 200 or acquired from various information sources (e.g., AIS data 152, TLE data 153). The random forest method combines the output of multiple decision trees to reach a single result and is well suited for classification and regression problems. In embodiments utilizing random forest algorithms, the preprocessed dataset may be split into multiple subsets using a bagging or bootstrap aggregation, technique wherein a random subset of the entire training dataset is selected. Each individual decision tree is generated from a different selected random subset with replacement known as row sampling. This step of row sampling with replacement is referred to as bootstrap. Each decision tree is trained independently and generates output. The final output may be based on majority (or averaging) voting after combining the results of all models via aggregation. Examples of hyperparameters for random forest models that may be tuned via parametric optimizer 305 can include (but not limited to) the number of trees the algorithm builds before aggregating the predictions, maximum number of features random forest considers splitting a node, minimum number of leaves required to split an internal node, how to split the node in each tree, and maximum leaf nodes in each tree, and/or the like.

Figure 4:
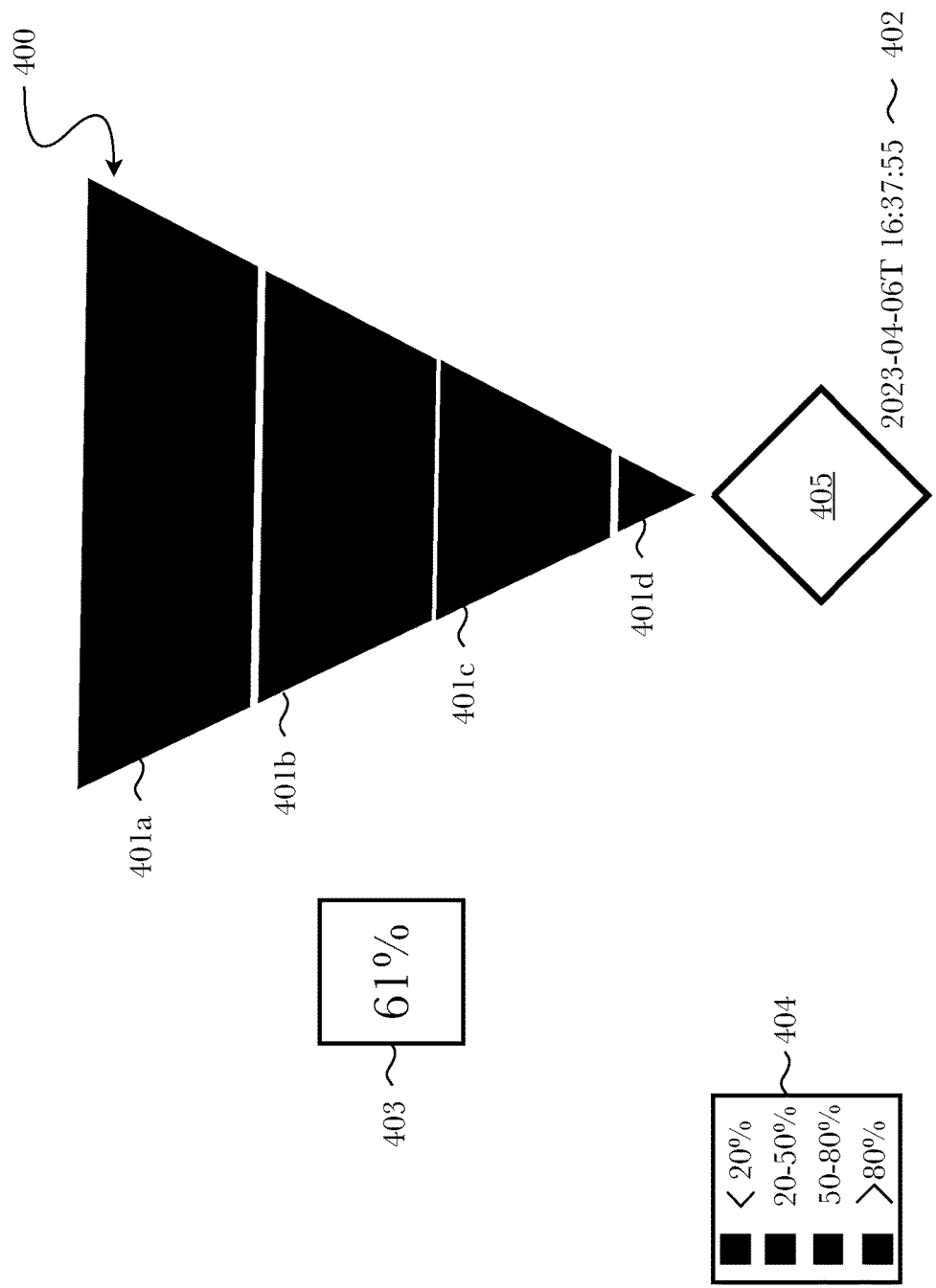
FIG. 4 is an example of a target of interest with its associated cone of trajectory split into cone slices and displaying metadata as well as the computed average score for the entire cone.

FIG. 4 is an example of a target of interest 405 with its associated cone of trajectory 400 split into cone slices 401a-d and displaying metadata 402 as well as the computed average score 403 for the entire cone. According to the embodiment, a legend 404 may be present which indicates the color of cone slice and what confidence score it has. Each cone slice 401a-d may be color coded wherein the color indicates the confidence score for that slice of the cone of trajectory for the target of interest. The target of interest 405 is represented as a diamond but may take on any shape or color according to the embodiment. Metadata 402 can include information about the date and time associated with the displayed target of interest. This information may be sent to and displayed by data presentation layer 120 of target custody platform 100. In some embodiments, the information displayed in FIG. 4 may be overlayed on top of a map of the region. For example, if the target of interest was a ship, then the information may be displayed on a map of the body of water the ship is sailing on and any nearby land masses, islands, etc.

Detailed Description of Exemplary Aspects

Figure 5:
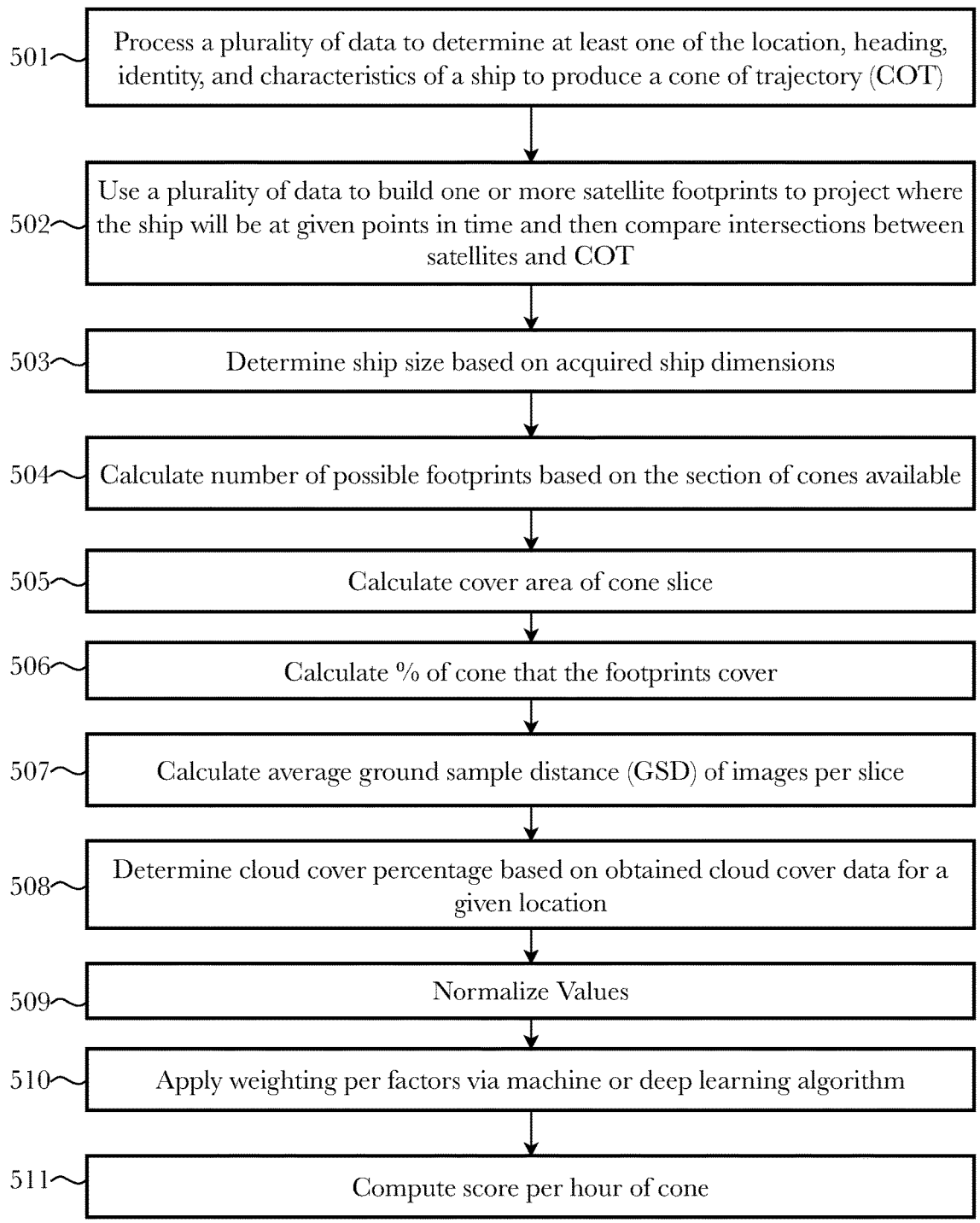
FIG. 5 is a flow diagram illustrating an exemplary method 500 for modeling target of interest navigation channels with confidence intervals, according to an embodiment.

FIG. 5 is a flow diagram illustrating an exemplary method 500 for modeling target of interest navigation channels with confidence intervals, according to an embodiment. In this exemplary use case, the target of interest is a sailing vessel. According to the embodiment, the method can utilize automated identification system (AIS) emissions as the seed for developing a target tracking model. In some implementations, feasibilities were run for all major Commercial Imagery vendors, and image footprints calculated from the imagery data obtained from satellites. Image footprint metadata that is a geo-temporal correlation to a sector of the trajectory are aggregated to produce a likelihood score. In some implementations, likelihood is derived based on the intended target size, percentage of the sector covered by imagery, number of images, average ground sample distance (GSD), and percentage of cloud cover.

According to the embodiment, the process begins at step 501 when target custody platform 100 processes a plurality of obtained data to determine at least one of a location, heading, identity, and characteristics of a ship to produce a cone of trajectory (COT). In some implementations, the obtained data may comprise at least automatic identification system data. In this step, obtained AIS data may be parsed and processed to identify the features associated with one or more ships described above. As a next step 502, data analytics engine 200 can use the plurality of obtained data to build one or more satellite footprints to project where the ship will be at given points in time and then compare intersections between satellites and the COT. As a next step 503, the size of the ship associated with the COT is determined using data parsed from the obtained AIS data. The ship dimensions of length and width can be sourced directly from AIS data and used to determine the ship size. As a next step 504, data analytics engine 200 can calculate the number of possible footprints based on the section of cones available. In various implementations, this calculation may be set to a time interval, for example, calculating the number of footprints per hour or half-hour. After the number of footprints has been calculated over a specified time interval, the next step 505 performed by data analytics engine 200 is to calculate the cover area of a cone slice. Further, data analytics engine 200 can use the calculated area of a cone slice as an input for calculating the percentage of the cone that the footprints cover at step 506. At a next step 507, platform 100 calculates the average ground sample distance (GSD) of received satellite images per slice. The next step 508, data analytics engine 200 determines cloud cover percentage based on obtained cloud cover data for a given location. As a next step 509, the quantities and characteristics determined, calculated, and/or computed in previous steps may be pre-processed and normalized prior to being used as inputs into one or more machine and/or deep learning algorithms configured to apply weighting factors 510 to each of the normalized values. As a last step 511, the trained one or more machine and/or deep learning models may produce as output, responsive to the input of the normalized value, a likelihood score per hour of cone.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 6:
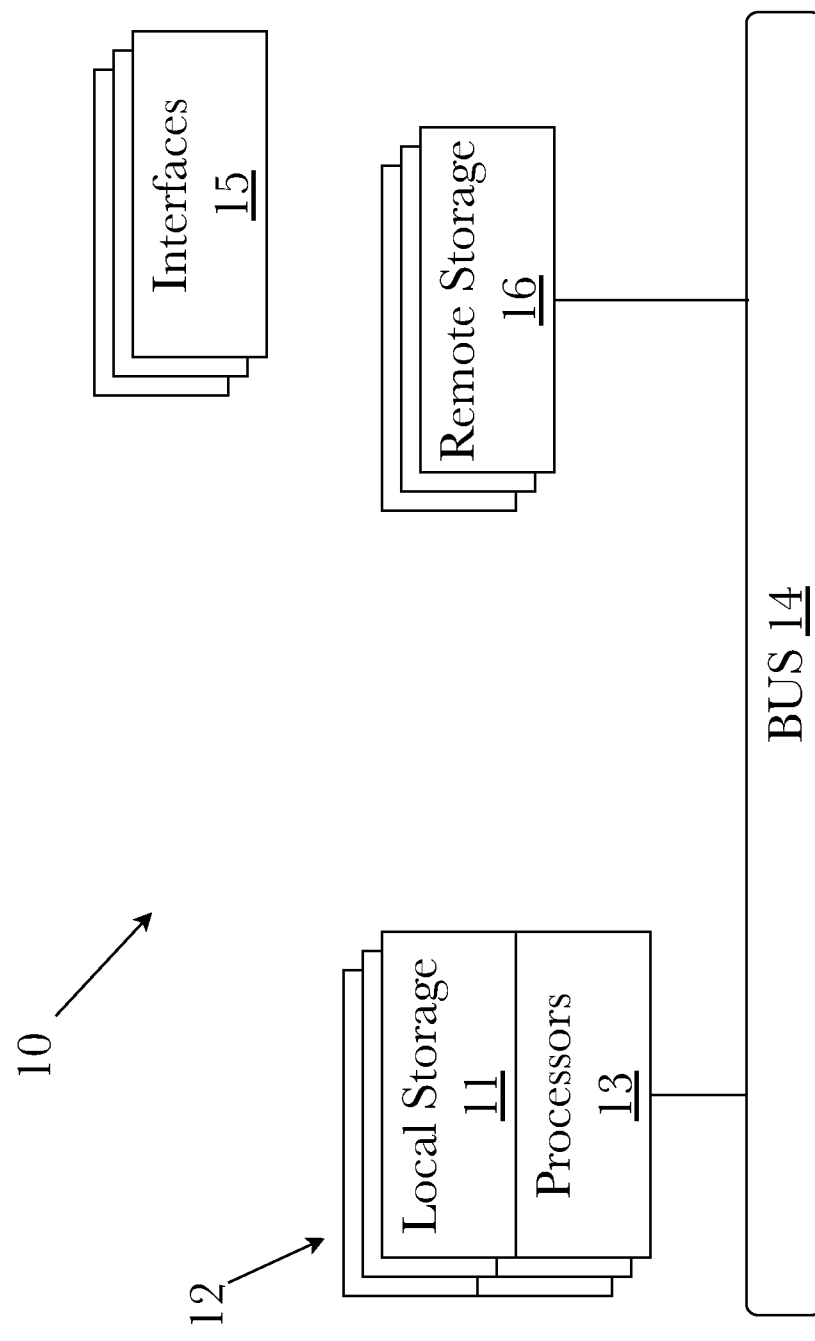
FIG. 6 is a block diagram illustrating an exemplary hardware architecture of a computing device.

Referring now to FIG. 6, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™ THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 6 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 7:
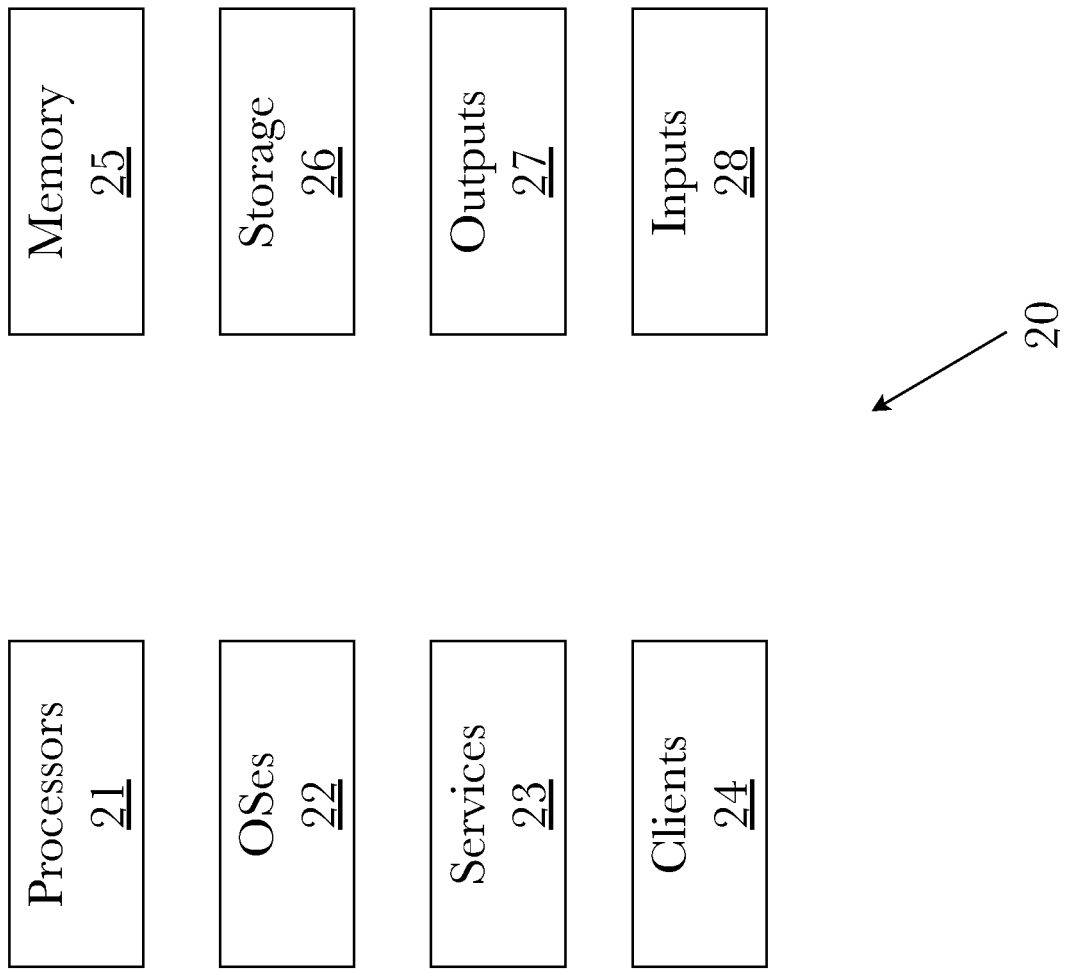
FIG. 7 is a block diagram illustrating an exemplary logical architecture for a client device.

In some aspects, systems may be implemented on a standalone computing system. Referring now to FIG. 7, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20 and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 6). Examples of storage devices 26 include flash memory, magnetic hard drive, CD-ROM, and/or the like.

Figure 8:
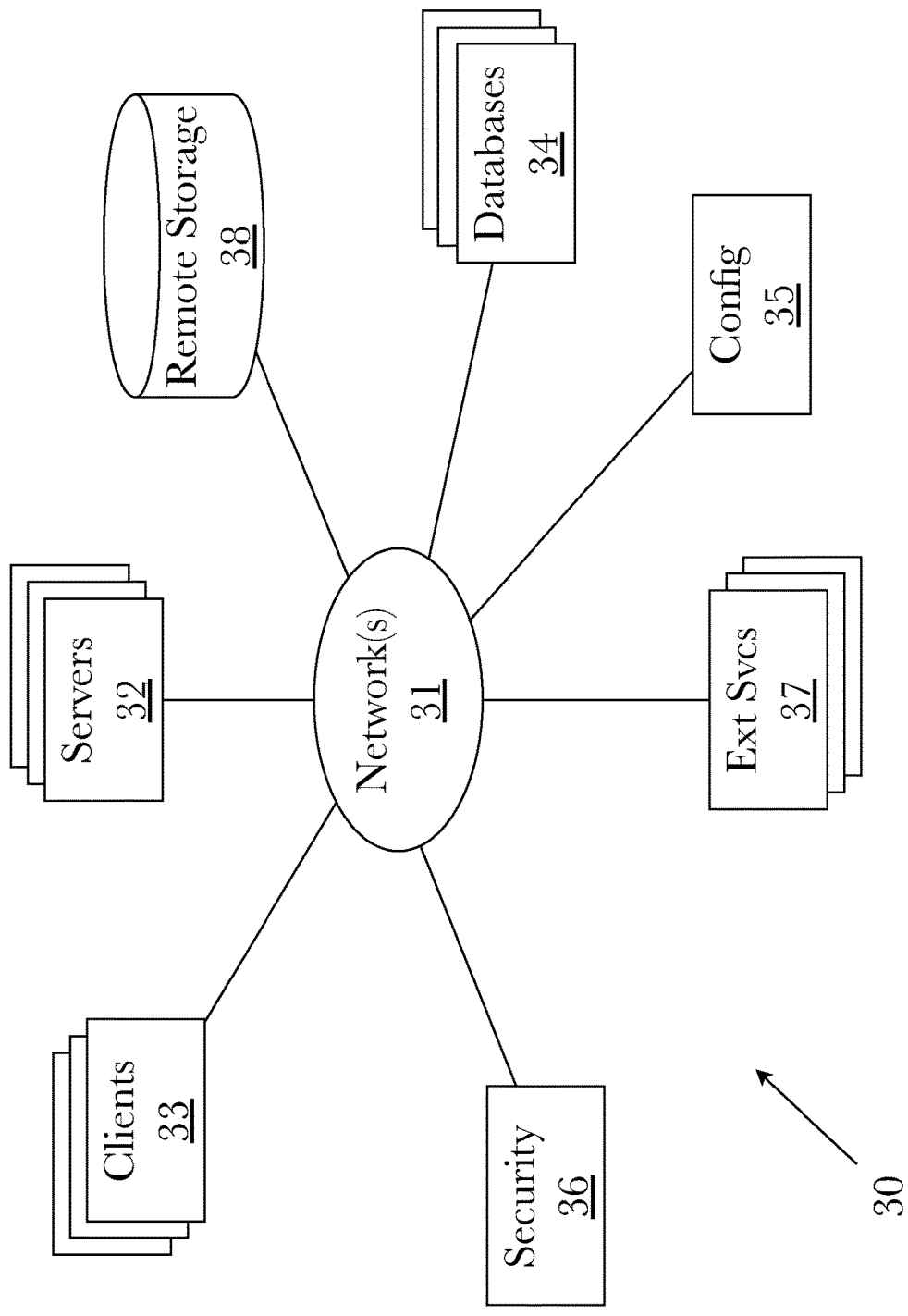
FIG. 8 is a block diagram showing an exemplary architectural arrangement of clients, servers, and external services.

In some aspects, systems may be implemented on a distributed computing network, such as one having any number of clients and/or servers. Referring now to FIG. 8, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 7. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 9:
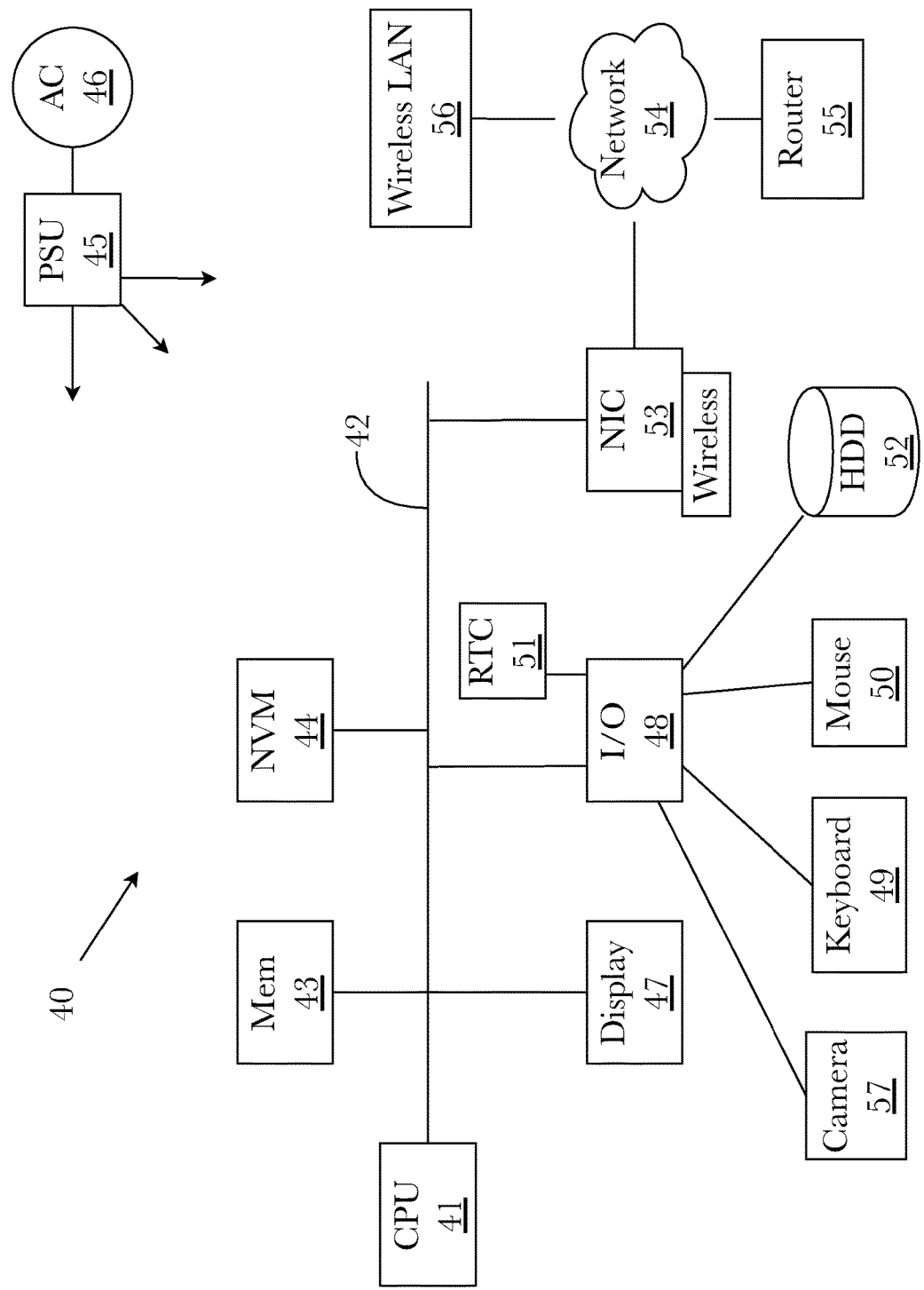
FIG. 9 is another block diagram illustrating an exemplary hardware architecture of a computing device.

FIG. 9 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router wireless local area network 56, or any other network connection. Also shown as part of system is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A target custody platform, comprising:
   a computing device comprising a memory and a processor;
   an analysis engine comprising a first plurality of programming instructions stored in the memory which, when operating on the processor, causes the computing device to:
   task a plurality of satellites with obtaining imagery data based on a projected path of a target of interest;
   build a plurality of satellite footprints using a subset of the imagery data;
   identify sections of the projected path where one or more of the satellite footprints intersect the projected path of the target of interest;
   for each identified section, calculate a cover area;
   calculate an amount of the projected path that the satellite footprints cover; and
   calculate an average ground sample distance based on a subset of the imagery data; and
   a machine learning algorithm configured to compute a confidence score for each of the identified sections based on input data comprising at least the plurality of satellite footprints, the identified sections, the calculated cover area for each section, the amount of the projected path that the satellite footprints cover, and the average ground sample distance.

2. The platform of claim 1, wherein the machine learning algorithm is a random forest algorithm.

3. The platform of claim 1, wherein the machine learning algorithm is a deep learning algorithm.

4. The platform of claim 3, wherein the deep learning algorithm is a neural network.

5. The platform of claim 1, wherein the analysis engine is further configured to:
   obtain a plurality of information associated with the target of interest from one or more external databases;
   determine a size of the target of interest based on the plurality of obtained information associated with the target; and wherein the size is used as an additional input into the machine learning algorithm.

6. The platform of claim 5, wherein the target of interest is a sailing vessel and wherein the information associated with the sailing vessel includes automated identification system data.

7. The platform of claim 5, wherein the target of interest is an airplane, a satellite, or a land vehicle.

8. The platform of claim 5, wherein each of the computed confidence scores for each of the identified sections are aggregated together to form an average confidence score for the entire projected path of the target of interest.

9. The platform of claim 1, wherein the analysis engine is further configured to:
obtain weather pattern data;
determine a cloud cover percentage based on the obtained weather pattern data; and
wherein the cloud cover percentage is used as an additional input into the machine learning algorithm.

10. The platform of claim 1, wherein the machine learning algorithm is a logistic regression algorithm.

11. A method for providing target custody, comprising the steps of:
tasking a plurality of satellites with obtaining imagery data based on a projected path of a target of interest;
building a plurality of satellite footprints using a subset of the imagery data;
identifying sections of the projected path where one or more of the satellite footprints intersect the projected path of the target of interest;
for each identified section, calculating a cover area;
calculating an amount of the projected path that the satellite footprints cover; and
calculating an average ground sample distance based on a subset of the imagery data; and
using a machine learning algorithm configured to compute a confidence score for each of the identified sections based on input data comprising at least the plurality of satellite footprints, the identified sections, the calculated cover area for each section, the amount of the projected path that the satellite footprints cover, and the average ground sample distance.

12. The method of claim 11, wherein the machine learning algorithm is a random forest algorithm.

13. The method of claim 11, wherein the machine learning algorithm is a deep learning algorithm.

14. The method of claim 13, wherein the deep learning algorithm is a neural network.

15. The method of claim 11, wherein the analysis engine is further configured to:
obtain a plurality of information associated with the target of interest from one or more external databases;
determine a size of the target of interest based on the plurality of obtained information associated with the target; and
wherein the size is used as an additional input into the machine learning algorithm.

16. The method of claim 15, wherein the target of interest is a sailing vessel and wherein the information associated with the sailing vessel includes automated identification system data.

17. The platform of claim 15, wherein the target of interest is an airplane, a satellite, or a land vehicle.

18. The platform of claim 15, wherein each of the computed confidence scores for each of the identified sections are aggregated together to form an average confidence score for the entire projected path of the target of interest.

19. The method of claim 11, wherein the analysis engine is further configured to:
obtain weather pattern data;
determine a cloud cover percentage based on the obtained weather pattern data; and
wherein the cloud cover percentage is used as an additional input into the machine learning algorithm.

20. The platform of claim 11, wherein the machine learning algorithm is a logistic regression algorithm.

* * * * *